US010337970B2

(12) United States Patent
Zhang et al.

(10) Patent No.: US 10,337,970 B2
(45) Date of Patent: Jul. 2, 2019

(54) APPARATUS AND METHOD FOR IN-SITU TESTING IMPACT STRENGTH OF MICRO-STRUCTURE

(71) Applicant: PEKING UNIVERSITY, Beijing (CN)

(72) Inventors: Li Zhang, Beijing (CN); Dacheng Zhang, Beijing (CN); Fang Yang, Beijing (CN); Wei Wang, Beijing (CN); Dayu Tian, Beijing (CN); Peng Liu, Beijing (CN); Ting Li, Beijing (CN); Kui Luo, Beijing (CN)

(73) Assignee: PEKING UNIVERSITY, Beijing (CN)

( * ) Notice: Subject to any disclaimer, the term of this patent is extended or adjusted under 35 U.S.C. 154(b) by 0 days.

(21) Appl. No.: 15/579,397

(22) PCT Filed: Jun. 5, 2015

(86) PCT No.: PCT/CN2015/080872
§ 371 (c)(1),
(2) Date: Dec. 4, 2017

(87) PCT Pub. No.: WO2016/192100
PCT Pub. Date: Dec. 8, 2016

(65) Prior Publication Data
US 2018/0149568 A1 May 31, 2018

(51) Int. Cl.
*G01N 3/00* (2006.01)
*G01N 3/307* (2006.01)
(52) U.S. Cl.
CPC ....... *G01N 3/307* (2013.01); *G01N 2203/001* (2013.01); *G01N 2203/0035* (2013.01);
(Continued)
(58) Field of Classification Search
CPC .... G01N 3/307; G01N 3/00; G01N 2203/001; G01N 2203/0067; G01N 2203/0208;
(Continued)

(56) References Cited

U.S. PATENT DOCUMENTS 4,139,814 A * 2/1979 Radd .................. G01N 17/00
                                                    324/464
2002/0189357 A1* 12/2002 Lai .................. B81C 99/005
                                                    73/584
(Continued)

FOREIGN PATENT DOCUMENTS

| CN | 1936535 | 3/2007 |
| CN | 104330236 | 2/2015 |
| ES | 2176090 | 11/2002 |
| GB | 190825470 | 11/1909 |

(Continued)

OTHER PUBLICATIONS

International Search Report, issued in the corresponding PCT application No. PCT/CN2015/080872, dated Mar. 10, 2016, 4 pages.
Extended European Search Report, issued in the corresponding European patent application No. 15893756.5, dated Jan. 22, 2019, 7 pages.

*Primary Examiner* — Max H Noori
(74) *Attorney, Agent, or Firm* — Hamre, Schumann, Mueller & Larson, P.C.

(57) ABSTRACT

An apparatus and a method for in-situ testing impact strength of a micro-structure are provided. In one embodiment, the apparatus includes: a flexible beam, one end of which being fixed; an impact mass block disposed at the other end of the flexible beam and being for exerting an impact on the micro-structure; and a locking member including a beam arm and a plurality of locking teeth. The beam arm is perpendicular to the flexible beam and one end of the beam arm is fixed, and the plurality of locking teeth are distributed at intervals along the beam arm, such that the other end of the flexible beam is engaged to one of the plurality of locking teeth when the flexible beam is loaded.

20 Claims, 3 Drawing Sheets

(52) U.S. Cl.
CPC ............... *G01N 2203/0039* (2013.01); *G01N 2203/0067* (2013.01); *G01N 2203/0087* (2013.01); *G01N 2203/0208* (2013.01); *G01N 2203/0244* (2013.01); *G01N 2203/0248* (2013.01); *G01N 2203/0286* (2013.01); *G01N 2203/0605* (2013.01); *G01N 2203/0682* (2013.01)

(58) Field of Classification Search
CPC ... G01N 2203/0244; G01N 2203/0248; G01N 2203/0605; G01N 2203/0682
USPC .......................................................... 73/788
See application file for complete search history.

(56) References Cited

U.S. PATENT DOCUMENTS

| | | | | |
|---|---|---|---|---|
| 2009/0145230 A1* | 6/2009 | Ikeuchi | .............. | G01C 19/5719 73/514.32 |
| 2012/0243004 A1* | 9/2012 | El Gawhary | .......... | G01B 11/24 356/601 |

FOREIGN PATENT DOCUMENTS

| | | |
|---|---|---|
| JP | 2005-207873 | 8/2005 |
| JP | 5621478 | 11/2014 |

* cited by examiner

APPARATUS AND METHOD FOR IN-SITU TESTING IMPACT STRENGTH OF MICRO-STRUCTURE

BACKGROUND OF THE INVENTION

Field of the Invention

The present disclosure relates to the machining field of the micro-electromechanical systems (MEMS), and particularly, relates to an apparatus and a method for in-situ testing impact strength of micro-structure.

Description of the Related Art

The micro-electromechanical system is an important trend of development and application of the micro electronic technology. Now, various MEMS sensors are widely applied in many aspects of the home application and the military application, and devices using such sensors, such as a pressure meter, an accelerometer, a gyroscope and so on, are essential components in consumer electronics and high precision applications. Due to the physical parameters being measured, the MEMS sensors are usually used in a shock environment, so the impact strength of the structure of the sensors is a key issue for these sensors. The conventional method for evaluating impact strength of the MEMS sensors is drop test, which requires the sensor to be slivered and packaged after the whole manufacturing process, thus it is difficult to test the strength of the device immediately, thus greatly extending the whole designing process and cycle. At the same time, such conventional method for evaluating impact strength is relatively destructive, and the sensor chip will have a large area of structural failures after such conventional testing method, thus it is difficult to find out the weakest portion in the structure during the impact. Furthermore, limited by the manner of loading, the conventional method for evaluating impact strength cannot get a load with a high impact peak value (greater than 100000 g) and a large impact pulse width (s magnitude). However, such austere impact environment is very common in actual military applications. Thus, the conventional method for evaluating impact strength and apparatus thereof have obvious limitations.

SUMMARY OF THE INVENTION

Therefore, the object of the present disclosure is intended to overcome at least one of the above mentioned problems or defects existed in the prior art.

In one aspect of the present disclosure, the present disclosure provides an apparatus for in-situ testing impact strength of micro-structure, comprising a flexible beam, one end of which being fixed; an impact mass block, disposed at the other end of the flexible beam and configured to exert an impact on a micro-structure; and a locking member, including a beam arm and a plurality of locking teeth, wherein one end of the beam arm is fixed, and the plurality of locking teeth are distributed at intervals along the beam arm, such that the other end of the flexible beam is engaged to one of the plurality of locking teeth when the flexible beam is loaded.

In another aspect, the present disclosure also provides a method for in-situ testing impact strength of a micro-structure, comprising: (a) fixing the micro-structure at one end so that the micro-structure faces an impact mass block; (b) loading the flexible beam such that the other end of the flexible beam is engaged to one of the plurality of locking teeth closest to the other end of the flexible beam; (c) releasing the other end of the flexible beam so as to impact the micro-structure through the impact mass block provided on the other end of the flexible beam; (d) repeating steps (b) and (c), such that the other end of the flexible beam is engaged to every tooth of the plurality of locking teeth in an order from the nearest tooth to the farthest tooth and is released, until the micro-structure is damaged; and (e) recording the position of the corresponding locking tooth when the micro-structure is damaged, calculating corresponding load-deflection and obtaining corresponding impact strength.

BRIEF DESCRIPTION OF THE DRAWINGS

FIG. 3($b$) is an schematic view of impact speed of the apparatus for in-situ testing impact strength of micro-structure according to an exemplary embodiment of FIG. 3($a$) at different loading conditions and simulated by ansys software (ansys inc. America); and FIG. 3($c$) is an schematic view of impact stress peak caused to the micro-structure by the apparatus for in-situ testing impact strength of micro-structure according to an exemplary embodiment of FIG. 3($a$) at different loading conditions and simulated by ansys software (ansys inc. America).

DETAILED DESCRIPTION OF PREFERRED EMBODIMENTS OF THE INVENTION

Embodiments of the present disclosure will be explained in detail with reference to the drawings to make the configuration, advantages and effects apparent to the skilled person in the art.

The present disclosure can also be implemented or applied by other embodiments, and every detail in the description can be modified and changed on basis of different views and applications without departing from the concept and scope of the present disclosure.

According to a general concept of the present disclosure, an apparatus and a method for in-situ testing impact strength of micro-structure is designed. Specifically, while functional device with such micro-structure is manufactured, the functional device and the apparatus for in-situ testing impact strength of the micro-structure according to the present disclosure are manufactured on a silicon wafer with the functional device at the same time by the standard silicon on glass (SOG) bonding bulk silicon process (i.e. adding a testing area with the apparatus for in-situ testing impact strength of micro-structure according to the present disclosure onto the silicon wafer), meanwhile, a test simple of the micro-structure used in a later impact strength testing is manufactured at the apparatus under the same manufacturing conditions. After the functional device, the apparatus, and the test simple of the micro-structure are manufactured, an impact is applied on the test simple of the micro-structure by the apparatus, thus the impact strength test is performed and parameters of mechanical properties of the functional device can be achieved on line.

Figure 1:
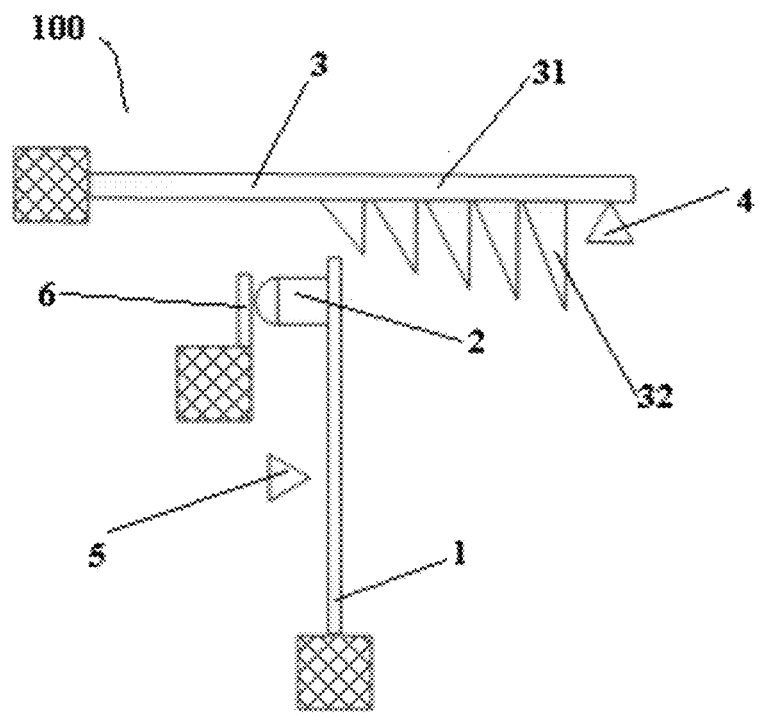
FIG. 1 is a schematic view of an apparatus for in-situ testing impact strength of micro-structure according to an embodiment of the present disclosure, wherein the flexible beam is not loaded.
Figure 2:
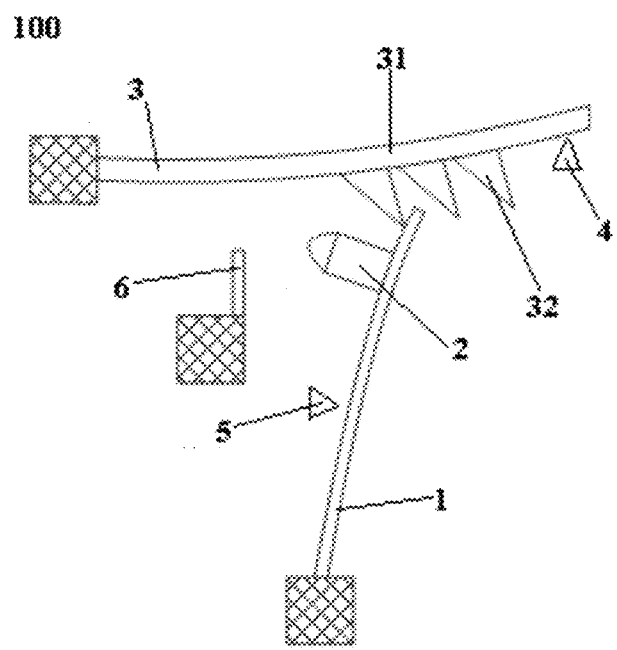
FIG. 2 is a schematic view of an apparatus for in-situ testing impact strength of micro-structure according to an embodiment of the present disclosure, wherein the loaded flexible beam is being released, and wherein one end of the flexible beam is engaged to one of the plurality of locking teeth when the flexible beam is loaded.

Referring to FIGS. 1 and 2, the apparatus 100 for in-situ testing impact strength of micro-structure according to an embodiment of the present disclosure comprises: a flexible beam 1, one end of which being fixed; an impact mass block 2, disposed at the other end of the flexible beam 1 and configured to exert an impact on a micro-structure; and a locking member 3, including a beam arm 31 and a plurality of locking teeth 32, wherein the beam arm 31 is perpendicular to the flexible beam 1, one end of the beam arm 31 being fixed, and the plurality of locking teeth 32 being distributed at intervals along the beam arm 31, such that the other end of the flexible beam 1 is engaged to one of the plurality of locking teeth 32 when the flexible beam 1 is loaded.

In the apparatus for in-situ testing impact strength of micro-structure according to embodiments of the present disclosure, a width w and a length l of the flexible beam 1 determines the maximum impact energy created by the apparatus on the follow equation (1):

$$PE = \frac{2\delta_{max}^2 lI}{3w_{max}^2 E} \quad (1)$$

where $\delta_{max}$ is a static tensile fracture strength of silicon, l is a length of beam, w is a width of beam, E is a Young modulus of silicon, I is an inertia moment of beam. The size and shape of the impact mass block 2 determine a scale of impact energy of the apparatus transmitted to the micro-structure, and the distribution of the locking teeth 32 along the beam arm determines the minimum resolution of the impact strength testing of the whole apparatus.

At the time of testing, the micro-structure to be tested is provided at one end of the flexible beam 1 provided with the impact mass block 2, as shown in FIG. 1. When the flexible beam is loaded, the end of the flexible beam provided with the impact mass block 2 is engaged to one of the plurality of locking teeth 32 by pushing the flexible beam 1 and/or beam arm 31. Subsequently, a free end of the beam arm 31 is continuously pushed until the end of the flexible beam 1 provided with the impact mass block 2 is released from the engaged locking tooth, and instant impact is exerted on the micro-structure 6.

Compared with conventional testing method in which the whole functional device is impacted, such as sensors, the apparatus for in-situ testing impact strength of micro-structure of the present disclosure may test impact strength of the micro-structure more conveniently and accurately, which obviously shortens testing time, and is more helpful to feedback in design of the functional device such as sensors. Furthermore, since micro-structures may be tested, a complex structure may be divided into various micro-structures which may be tested one by one, thus the weakest area of the complex structure may easily be found.

In an embodiment, the apparatus 100 for in-situ testing impact strength of micro-structure of the present disclosure, the micro-structure 6 to be tested and a functional device (not shown in the drawings. such as sensor, etc.) are manufactured by the standard silicon on glass (SOG) bonding bulk silicon process, wherein the micro-structure 6 to be tested is a replicated sample of a micro-structure of the functional device, to perform the impact strength testing. During manufacturing process, patterns of the micro-structure 6, the apparatus 100 and the functional device are formed in the same photolithography process, and the movable silicon structures of the micro-structure, the apparatus, and the functional device are released in the same etching process. As such, it's ensured that the micro-structure 6 to be tested and the actual working functional device such as a sensor, have consistent impact strength, and interference caused by process errors is eliminated.

In an embodiment, the apparatus 100 for in-situ testing impact strength of micro-structure of the present disclosure, the micro-structure 6 to be tested and a functional device (not shown in the drawings. such as a sensor, etc.) are manufactured by the standard silicon on glass (SOG) bonding bulk silicon process, such that the apparatus 100, the micro-structure 6 to be tested and the functional device are formed in the same micro unit, facilitating individual testing of every functional device. Through such configuration, at one hand, it is possible to perform an impact strength testing on each functional device; on the other hand, on the other hand, since a functional device such as a sensor is separated from a test area, the impact strength of the micro-structure could be tested on line, without damaging the actual working functional device, thus being superior to a traditional impact manner by which the entire functional device is damaged.

In an embodiment, the apparatus 100 for in-situ testing impact strength of micro-structure of the present disclosure, the micro-structure 6 to be tested and the functional device (not shown in drawings. such as a sensor, etc.) are manufactured by the standard silicon on glass (SOG) bonding bulk silicon process, such that the micro-structure 6 is anchored on the silicon wafer (not shown) on which the functional device are provided, and is faced to the impact mass block 2, and, one end of the flexible beam 1 and one end of the beam arm 31 are anchored on the silicon wafer.

In an embodiment, a plurality of locking teeth 32 are sequentially distributed at intervals along the beam arm 31 from the free end of the beam arm 31 and lengths of the teeth are reduced by an equal amount. However, the present disclosure is not limit thereto. The skilled person in the art may set the interval and tooth length of every locking teeth and number of the locking teeth according to actual testing resolution requirement. For example, in a preferred embodiment, locking teeth 32 are distributed at equal intervals and a line connecting each tooth tip forms a generally circular arc profile, as shown in FIG. 1.

In an embodiment, size of the impact mass block 2 is set to be substantially consistent with that of the micro-structure 6. The size and shape of the impact mass block 2 may be changed with the size and shape of the micro-structure 6, thus, an impact load with high acceleration and high pulse width can be achieved. For example, in a preferred embodiment, one end of the impact mass block 2 is arc-shaped, as shown in FIGS. 1 and 2. However, the present disclosure is not limited thereto. The skilled person in the art can select the shape and size of the impact mass block 2 based on actual requirements, also can adjust the size of the impact mass block and the flexible beam simultaneously to obtain the impact load required.

In an embodiment, the apparatus 100 for in-situ testing impact strength of micro-structure of a the present disclosure includes a first probe 4 for pushing the free end of the beam arm 31 so as to load and/or release the free end of the flexible beam 1 engaged to one of the plurality of locking teeth 32. In an embodiment, the apparatus 100 for testing impact strength of micro-structure of the present disclosure also includes a second probe 5 for pushing the free end of the flexible beam 1 so as to engage to one of the plurality of locking teeth 32. It should be noted that the present disclosure is not limited thereto, the skilled person in the art can select any proper structure based on actual requirements as long as the flexible beam 1 and the beam arm 32 are pushed to load and/or release the flexible beam.

In addition, the present disclosure also provides a method for in-situ testing impact strength of the micro-structure by the apparatus 100, comprising the following steps: (a) fixing a micro-structure 6 so that the micro-structure faces an impact mass block; (b) loading the flexible beam 1 such that the other end (that is, the free end) of the flexible beam 1 is engaged to one of the plurality of locking teeth 32 closest to the other end of the flexible beam 1; (c) releasing the other end of the flexible beam 1 so as to impact the micro-structure 6 through the impact mass block 2 provided at the other end of the flexible beam 1; (d) repeating steps (b) and (c), such that the other end of the flexible beam 1 is engaged to every tooth of the plurality of locking teeth 32 in the order from the nearest tooth to the farthest tooth and is released, until the micro-structure 6 is damaged; and (e) recording the position of the corresponding locking tooth when the micro-structure is damaged, and calculating corresponding load-deflection and obtaining corresponding impact strength.

Compared with conventional testing method of impacting the whole functional device, such as a sensor, the apparatus for in-situ testing impact strength of micro-structure of the present disclosure may test impact strength of the micro-structure more conveniently and accurately, which obviously shortens testing time, and is more helpful to feedback in design of the functional device such as sensors. Furthermore, since micro-structures may be tested, a complex structure may be divided into various micro-structures which may be tested one by one, thus the weakest area of the complex structure may easily be found.

In an embodiment, the step (a) comprises: by the standard silicon on glass (SOG) bonding bulk silicon process, patterns of the micro-structure 6, the apparatus 100 and the functional device are formed in the same photolithography process, and the movable silicon structures of the micro-structure, the apparatus, and the functional device are released in the same etching process, such that micro-structure is anchored on the silicon wafer on which the functional device are provided and is faced to the impact mass block, and one end of the flexible beam and one end of the beam arm are anchored on the silicon wafer.

In an embodiment, the step (c) comprises: pushing the free end of the beam arm 31 by a first probe 4 so as to load and/or release the other end of the flexible beam 1. In another embodiment, the step (b) comprises: pushing the other end (i.e. the free end) of the flexible beam 1 by a second probe 5 to load and/or release the other end of the flexible beam 1.

In an embodiment, in step (e), building a mechanical model of the apparatus by LS-DYNA simulator of ansys software (ANSYS inc. America) which is a commercially available large general software of finite element analysis, inputting the corresponding load-deflection into the mechanical model of the apparatus, obtaining acceleration value at the time of instant impact through simulation, and thus obtaining impact strength at the time of instant impact between the impact mass block and the micro-structure.

Figure 3A:
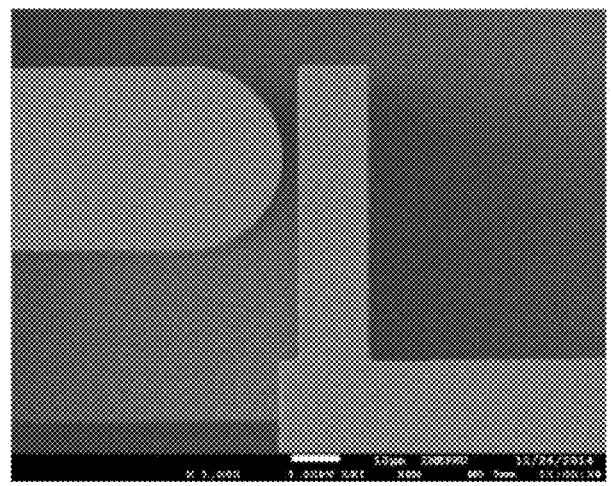
FIG. 3($a$) is a local schematic view of electronic microscope photograph of the apparatus for in-situ testing impact strength of micro-structure according to an exemplary embodiment of the present disclosure.
Figure 3B:
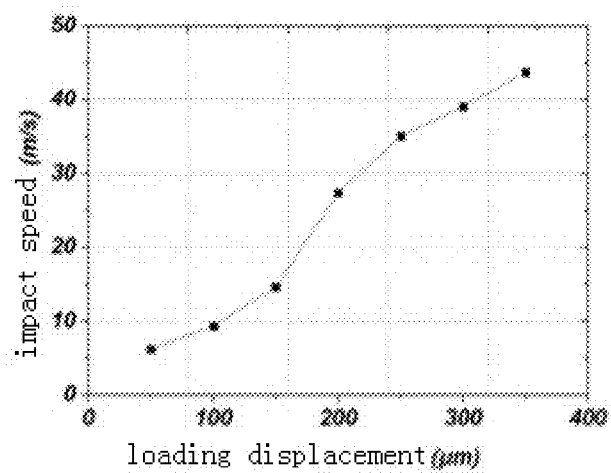
Figure 3C:
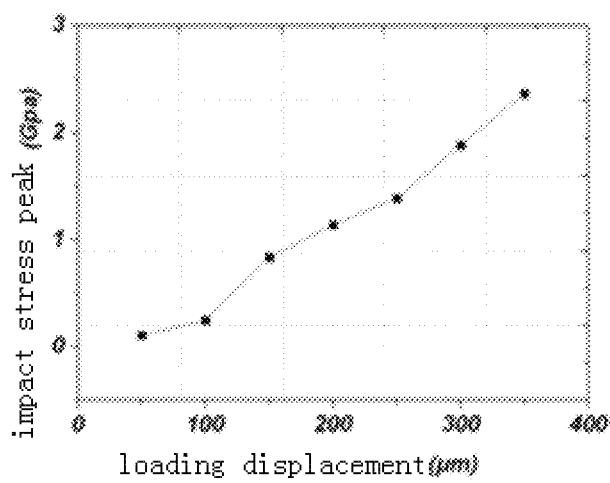

Next, an embodiment of the apparatus and method for in-situ testing impact strength of micro-structure of the present disclosure are described in detail with reference to FIGS. 3(a)-3(c).

Firstly, a size of the apparatus for in-situ testing impact strength of micro-structure of the present disclosure is determined by the micro-structure to be tested. In the present embodiment, the micro-structure to be test is formed as a single tooth structure with a width of 20 micrometers and a length of 40 micrometers. The size of the impact mass block 2 is similar with that of the micro-structure to be tested, that is, the impact mass block 2 is formed as a cube with an arc shape at a single side with a length of 40 micrometers and a width of 30 micrometers, as shown in the local schematic view of electronic microscope photograph of FIG. 3(a). A size of the flexible beam 1 is required to be designed to ensure that the speed of the impact mass block is up to 10 m/s at a moment before impacting the micro-structure to be tested. Thus, on the basis of energy storage equation of the flexible beam, relationship between the angular velocity and linear velocity, and the principle of conservation of energy, in the present embodiment, the size of the flexible beam is 700 micrometers long and 10 micrometers wide. Under such design, the instantaneous speed of the impact mass block at the moment before impact may be up to 20 m/s. The design of locking teeth is determined on the basis of impact speed resolution requirement, the higher the resolution, the more intensive the locking teeth are arranged, that is, the number of the locking teeth is larger. In this example, the interval between the teeth is 10 micrometers. Meanwhile, the position of the locking teeth varies depending on the flexible beam. In the present embodiment, the locking position where the flexible beam is loaded is on a ¼ circular sector contour formed by a radius of the flexible beam with the center being the end of the flexible beam, thus ensuring that the flexible beam is not blocked during a loading process.

In an embodiment, the micro-structure 6, the apparatus 100 and the functional device such as sensors are manufactured by the standard silicon on glass (SOG) bonding bulk silicon process, all of which are formed in the same micro unit, patterns of which are defined in the same photolithography process, and also movable silicon structures are formed in the same etching process.

After the manufacturing process is completed, the apparatus for in-situ testing impact strength of a micro-structure according to the present embodiment is loaded and tested, for example, by probes. In this embodiment, a probe (eg, a second probe) is directly driven to load the flexible beam into the position of the corresponding locking tooth in an order from the nearest to the farthest, and then a locking operation is performed through another probe (eg, a first probe). After the whole system is stable, the flexible beam is released through the other probe, the impact result is recorded, and the test is repeated until the micro-structure to be tested is destructed by impact load. Then loading distance of the flexible beam is recorded, that is, the position of the locking tooth at this moment. In this embodiment, the destruction location is the twentieth locking tooth, that is, the load-deflection is 200 microns.

Then, the impact failure deflection obtained by the test is inputted into the mechanical model built by the Ansys software of ANSYS Inc. (America), the impact process is simulated by the LS-DYNA module of the ANSYS software, and instantaneous impact acceleration of the impact between the impact mass block and the micro-structure under test in the condition that the deflection is 200 micrometers is obtained, which is the impact load ultimate strength value of the micro-structure under test. FIGS. 3(b) and 3(c) show an impact speed schematic view and a schematic view of impact stress peak caused to the micro-structure at different loading conditions. In this example, the impact strength of the micro-structure under tested is 1.25 Gpa.

The embodiments of the present disclosure described above illustrate the principle and the functions of the present disclosure by way of example only, rather than to limit the present disclosure. Those skilled in the art should understand that, without departing from the spirit and scope of the present disclosure, any changes and modifications to the disclosure are within the scope of the disclosure. The protection scope of the present disclosure should be as defined in the applied scope of the present application.

The invention claimed is:

1. An apparatus for in-situ testing impact strength of a micro-structure, comprising:
a flexible beam, one end of which being fixed;
an impact mass block disposed at the other end of the flexible beam and configured to exert an impact on the micro-structure; and
a locking member comprising a beam arm and a plurality of locking teeth, wherein the beam arm is perpendicular to the flexible beam and one end of the beam arm is fixed, and wherein the plurality of locking teeth are distributed at intervals along the beam arm, such that the other end of the flexible beam is engaged to one of the plurality of locking teeth when the flexible beam is loaded.

2. The apparatus according to claim 1, wherein by the silicon on glass bonding bulk silicon process, patterns of the micro-structure, the apparatus and a functional device are formed in the same photolithography process, the functional device comprising the same structure with the micro-structure, and wherein the movable silicon structures of the micro-structure, the apparatus, and the functional device are released in the same etching process, such that micro-structure is anchored on a silicon wafer on which the functional device are provided and faces the impact mass block, and one end of the flexible beam and one end of the beam arm are anchored on the silicon wafer.

3. The apparatus according to claim 1, wherein the plurality of locking teeth are sequentially distributed at intervals along the beam arm from the free end of the beam arm and lengths of the teeth are reduced by an equal amount.

4. The apparatus according to claim 1, further comprising:
a first probe for pushing the other end of the beam arm so as to load and/or release the other end of the flexible beam engaged to one of the plurality of locking teeth.

5. An apparatus according to claim 4, further comprising
a second probe for pushing the other end of the flexible beam so that the other end of the flexible beam is engaged to one of the plurality of locking teeth.

6. The apparatus according to claim 1, wherein a size of the impact mass block is set to be substantially consistent with that of the micro-structure.

7. The apparatus according to claim 6, wherein one end of the impact mass block is arc-shaped.

8. A method for in-situ testing impact strength of a micro-structure using the apparatus according to claim 1, comprising:
(a) fixing the micro-structure at one end so that the micro-structure faces the impact mass block;
(b) loading the flexible beam such that the other end of the flexible beam is engaged to one of the plurality of locking teeth closest to the other end of the flexible beam;
(c) releasing the other end of the flexible beam so as to impact the micro-structure through the impact mass block provided on the other end of the flexible beam;
(d) repeating steps (b) and (c), such that the other end of the flexible beam is engaged to every tooth of the plurality of locking teeth in an order from the nearest tooth to the farthest tooth and is released, until the micro-structure is damaged; and
(e) recording the position of the corresponding locking tooth when the micro-structure is damaged, calculating corresponding load-deflection and obtaining corresponding impact strength.

9. The method according to claim 8, wherein step (a) comprises:
by the silicon on glass bonding bulk silicon process, patterns of the micro-structure, the apparatus and a functional device are formed in the same photolithography process, the functional device comprising the same structure with the micro-structure, and wherein the movable silicon structures of the micro-structure, the apparatus, and the functional device are released in the same etching process, such that micro-structure is anchored on the silicon wafer on which the functional device are provided and faces the impact mass block, and one end of the flexible beam and one end of the beam arm are anchored on a silicon wafer.

10. The method according to claim 8, wherein step (c) comprises:
pushing the free end of the beam arm by the first probe so as to load and/or release the other end of the flexible beam.

11. The method according to claim 10, wherein step (b) comprises: pushing the other end of the flexible beam by a second probe to load and/or release the other end of the flexible beam.

12. The method according to claim 8, wherein step (e) comprises: inputting corresponding load-deflection into a mechanical model of the apparatus, and obtaining acceleration value at the time of instant impact between the impact mass block and the micro-structure.

13. The apparatus according to claim 2, wherein the plurality of locking teeth are sequentially distributed at intervals along the beam arm from the free end of the beam arm and lengths of the teeth are reduced by an equal amount.

14. The apparatus according to claim 2, further comprising:
a first probe for pushing the other end of the beam arm so as to load and/or release the other end of the flexible beam engaged to one of the plurality of locking teeth.

15. The apparatus according to claim 3, further comprising:
a first probe for pushing the other end of the beam arm so as to load and/or release the other end of the flexible beam engaged to one of the plurality of locking teeth.

16. The apparatus according to claim 14, further comprising
a second probe for pushing the other end of the flexible beam so that the other end of the flexible beam is engaged to one of the plurality of locking teeth.

17. The apparatus according to claim 15, further comprising
a second probe for pushing the other end of the flexible beam so that the other end of the flexible beam is engaged to one of the plurality of locking teeth.

18. The method according to claim 9, wherein step (c) comprises:
pushing the free end of the beam arm by the first probe so as to load and/or release the other end of the flexible beam.

19. The method according to claim 18, wherein step (b) comprises:
pushing the other end of the flexible beam by a second probe to load and/or release the other end of the flexible beam.

20. The method according to claim 9, wherein step (e) comprises: inputting corresponding load-deflection into a mechanical model of the apparatus, and obtaining acceleration value at the time of instant impact between the impact mass block and the micro-structure.

* * * * *